United States Patent [19]
Dou et al.

[11] Patent Number: 5,828,450
[45] Date of Patent: Oct. 27, 1998

[54] SPECTRAL MEASURING APPARATUS AND AUTOMATIC ANALYZER

[75] Inventors: Xiaoming Dou; Toshio Takama, both of Kyoto, Japan

[73] Assignee: Kyoto Dai-Ichi Kagaku Co., Ltd., Kyoto, Japan

[21] Appl. No.: 680,347

[22] Filed: Jul. 17, 1996

[30] Foreign Application Priority Data

Jul. 19, 1995 [JP] Japan .................................... 7-206560

[51] Int. Cl.$^6$ .............................. G01J 3/44; G01N 21/65
[52] U.S. Cl. ................. 356/301; 250/458.1; 250/459.1; 250/461.1; 250/339.07; 422/68.1; 422/82.05; 422/82.01
[58] Field of Search ................ 422/68.1, 82.05, 422/82.01; 356/301, 318; 250/458.1, 459.1, 461.1, 339.07, 340, 341.1, 341.5; 436/171

[56] References Cited

U.S. PATENT DOCUMENTS

| | | |
|---|---|---|
| 3,204,105 | 8/1965 | Robinson . |
| 3,807,862 | 4/1974 | Hatzenbuhler . |
| 5,011,284 | 4/1991 | Tedesco . |
| 5,262,644 | 11/1993 | Maguire . |
| 5,553,616 | 9/1996 | Ham et al. ............................... 128/663 |
| 5,617,205 | 4/1997 | Dou et al. ............................... 356/301 |

*Primary Examiner*—Ponnathapura Achutamurthy
*Assistant Examiner*—P. Ponnaluri
*Attorney, Agent, or Firm*—Nikaido, Marmelstein, Murray & Oram LLP

[57] ABSTRACT

In order to make a Raman spectral measuring apparatus effective for measurement of a vital sample and attain miniaturization and weight reduction, a near infrared laser diode is employed as a light source, and a spectroscope for receiving Raman scattered light from the sample is formed by a polychrometer comprising a concave diffraction grating and a multichannel photodiode array. The Raman scattered light incident through an inlet slit is separated into its spectral components by the diffraction grating, and its spectra are simultaneously detected by the photodiode array over a prescribed wavelength region.

13 Claims, 16 Drawing Sheets

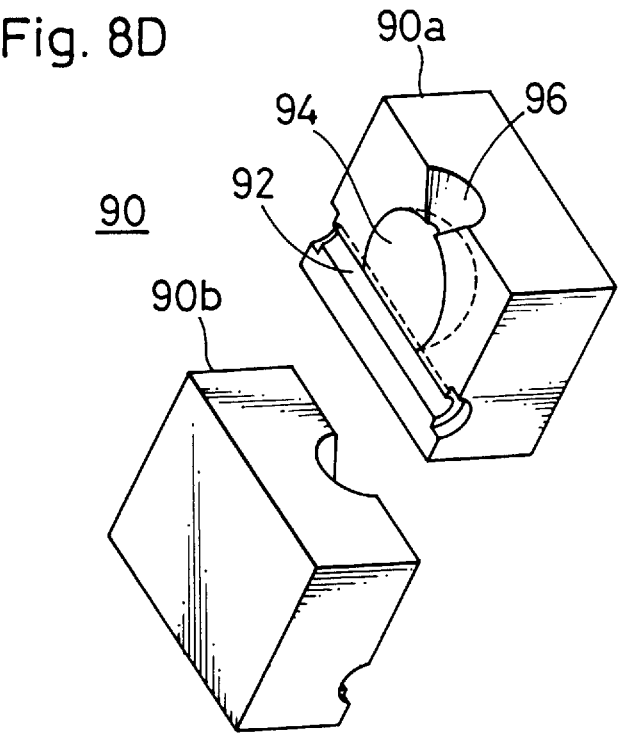
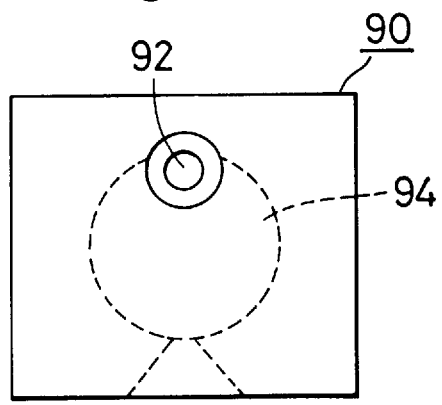
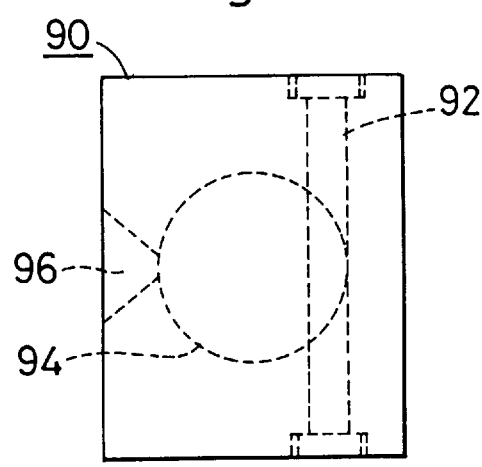
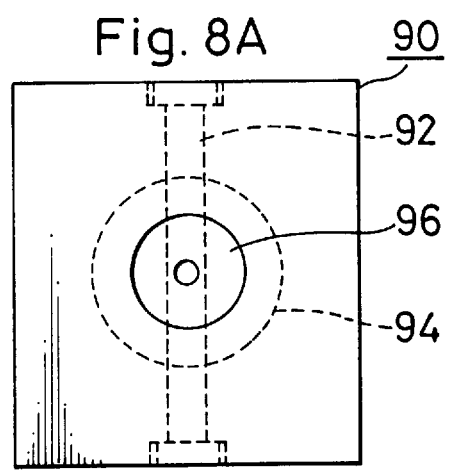

MEASURING OPERATION FLOW CHART (FIRST STEP)

MEASURING OPERATION FLOW CHART (SECOND STEP) IN CASE OF DISPOSABLE CELL

SPECTRAL MEASURING APPARATUS AND AUTOMATIC ANALYZER

BACKGROUND OF THE INVENTION

1. Field of the Invention

The present invention relates to a Raman scattering spectral measuring apparatus and an automatic analyzer comprising the same as a detecting part, and more particularly, it relates to a Raman scattering spectral measuring apparatus and an automatic analyzer which are suitable for measuring vital substances.

2. Description of the Background Art

Optical analyzing methods include a method called a Raman spectrometry. When certain molecules are illuminated, a small percentage of the molecules which have retained a photon do not return to their original vibration level after remitting the retained photon, but drops to a different vibrational level of the ground electronic state. The radiation emitted from these molecules will therefore be at a different energy and hence a different wavelength. This is referred to as Raman scattering.

If the molecule drops to a higher vibrational level of the ground electronic state, the photon emitted is at a lower energy or longer wavelength than that retained. This is referred to as Stokes-shifted Raman scattering. If a molecule is already at a higher vibrational state before it retains a photon, it can impart this extra energy to the remitted photon thereby returning to the ground state. In this case, the radiation emitted is of higher energy (and shorter wavelength) and is called anti-Stokes-shifted Raman scattering. In any set of molecules under normal conditions, the number of molecules at ground state is always much greater than those at an excited state, so the odds of an incident photon hitting an excited molecule and being scattered with more energy than it carried upon collision is very small. Therefore, photon scattering at frequencies higher than that of the incident photons (anti-Stokes frequencies) is minor relative to that at frequencies lower than that of the incident photons (Stokes frequencies). Consequently, it is the Stokes frequencies that are usually analyzed. Therefore, the energy released from these molecules is specific to these molecules, and the specific molecules can be identified by detecting the released energy as electromagnetic waves.

A Raman scattering spectral measuring apparatus is adapted to irradiate a sample provided in a sample part with excitation light which is emitted from a light source part, separate Raman scattered light from the sample into its spectral components in a photoreceiving part and detect the same, thereby measuring the concentrations of target components in the sample. Some such Raman scattering spectral measuring apparatuses have been proposed.

As a Raman scattering spectral measuring apparatus suitable for trace analysis, an apparatus employing a high-output laser diode as a light source for emitting excitation light, a photomultiplier which is sensitive to wavelengths of 800 to 1000 nm as a detector for detecting Raman scattered light, and a Michelson interferometer or a non-dispersive spectroscope such as a filter as a spectroscope for separating the Raman scattered light into its spectral components is proposed (Japanese Patent Laying-Open No. 5-256782 (1993); hereinafter refereed to as citation 1).

As another Raman scattering spectral measuring apparatus, an apparatus employing a gas laser unit such as an argon ion laser unit as an excitation light source, comprising a multidispersive spectroscope as a photoreceiving part for separating Raman scattered light into its spectral components and detecting the same, and employing a polychrometer comprising a one-dimensional line CCD as a detector is proposed (Japanese Patent Laying-Open No. 6-3271 (1994); hereinafter referred to as citation 2).

When a gas laser unit such as an Ar laser unit or an He-Ne laser unit or a solid-state laser unit such as a YAG laser is employed as the excitation light source, not only the volume of the light source part is increased but stability of the oscillation intensity is deteriorated and the cost is increased. Further, such a larger-sized unit consumes high energy.

When the interferometer employed in citation 1 or a scanning spectroscope is employed for separating the Raman scattered light from the sample into its spectral components, the volume is increased, reproducibility is deteriorated, and it is difficult to perform high-speed measurement.

When the multidispersive spectroscope described in citation 2 is employed, on the other hand, the volume as well as the cost are increased, and the light quantity is reduced to deteriorate the S/N ratio. The multidispersive spectroscope is practically too problematic to form a miniature measuring apparatus or be built into an automatic analyzer.

The wavelength region of an excitation light source which is generally employed in a Raman spectral measuring apparatus is visible to near infrared regions, in wavelengths of 380 to 800 nm. In consideration of measurement of a vital substance, however, the sample is readily damaged in a shorter wavelength region lower than 800 nm, due to high photon energy. Further, a general vital sample generates fluorescence, which is in the wavelength range of 650 to 800 nm. This wavelength range is substantially identical to a Raman shift wavelength range in case of making excitation with excitation light of a shorter wavelength region. When excitation is made with the excitation light of the shorter wavelength region, the quantum efficiency of fluorescence generation is increased to hide a Raman scattering signal of the vital sample. The quantum efficiency of Raman scattered light generation is increased when the excitation light is in a longer wavelength region under the same laser source power, and hence the conventional excitation wavelength region cannot be regarded as proper for performing Raman measurement for a vital sample at an excellent S/N ratio. As to the vital sample, the preferable excitation wavelength range is 800 to 1560 nm.

While there are many automatic analyzers comprising specimen dispensing mechanisms for dispensing specimens and reagent dispensing mechanisms for dispensing reagents and detecting reaction of reactive solutions of the specimens and the reagents, no analyzer utilizes a Raman spectral measuring apparatus as a detecting part for detecting reaction of a reactive solution.

SUMMARY OF THE INVENTION

A first object of the present invention is to provide a Raman spectral measuring apparatus comprising a light source generating excitation wavelength light effective for measurement of a vital sample and a detector having wavelength sensitivity capable of detecting Raman scattered light in such a wavelength region, which can be miniaturized and reduced in weight.

A second object of the present invention is to provide an automatic analyzer comprising such a Raman spectral measuring apparatus as a detecting part.

The Raman spectral measuring apparatus according to the present invention is adapted to irradiate a sample provided in a sample part with excitation light from a light source part, separate Raman scattered light from the sample into its spectral components and detect the same in a photoreceiving part thereby measuring the concentrations of target components in the sample, and comprises a near infrared semiconductor laser diode having an oscillation wavelength of 800 to 1560 nm as a light source of the light source part, while the photoreceiving part comprises a polychrometer comprising a single diffraction grating for separating the Raman scattered light from the sample into its spectral components and a detector having sensitivity for the near infrared region such as a multi-channel detector consisting of a Ge photodiode array or an InGaAs photodiode array for detecting the Raman scattered light separated into its spectral components by the diffraction grating. The apparatus further comprises a data processor for calculating the concentrations of the target components in the sample on the basis of detection signals from the photoreceiving part.

The apparatus preferably comprises an integrating sphere type scattered light reinforcing holder for making multiple reflection of the excitation light as a holder for holding a sample cell in the sample part, in order to improve Raman scattered light generation efficiency. The sample cell for making measurement through such an integrating sphere type scattered light reinforcing holder is preferably prepared from a flow cell or a disposable cell.

The automatic analyzer according to the present invention comprises the aforementioned Raman spectral measuring apparatus as its detecting part.

The near infrared semiconductor laser diode of the light source part can be prepared from AlGaAs, InGaAs or InGaAsP. When such a laser diode is employed, the cost as well as the space can be reduced, and a compact Raman spectral measuring apparatus can be implemented. While the oscillation intensity of the laser diode may be instabilized, such instability of the oscillation intensity can be corrected by detecting the light source intensity as a monitor and standardizing the detected intensity of Raman scattered light by the light source intensity.

The polychrometer employed in the photoreceiving part is a monodispersive spectrometer and hence its volume is small as compared with a multidispersive spectroscope while damping of the light quantity is small, whereby the overall Raman spectral measuring apparatus can be miniaturized while attaining cost reduction. The spectroscope may be transmission or reflection type diffraction grating.

When the near infrared region of 800 to 1560 nm is employed for the excitation wavelength, fluorescence is hardly generated from a vital substance, and the background of Raman scattered light measurement is reduced. Further, this region has small photon energy as compared with the visible region, and hence damage of the sample is reduced. Consequently, this region is suitable for measurement of a vital substance, due to smaller sample damage and smaller influence by fluorescence as compared with visible light excitation Raman spectroscopy.

A detector having sensitivity for the near infrared region such as a photo detective device of Ge, InGaAs, or Si is suitable for detecting Raman scattered light by excitation light of such a near infrared region. Multiwavelengths can be simultaneously detected by employing the multi-channel detector, and the Raman light intensity can be corrected by a light intensity of the excitation wavelength or a Rayleigh scattered light wavelength detected by employing parts thereof. Measuring accuracy is improved to be convenient for measurement of a minor sample by correcting fluctuation of the light source intensity.

The Raman spectral measuring apparatus according to the present invention comprises the near infrared semiconductor laser diode as the light source, whereby the cost as well as the space can be reduced, for implementing a compact Raman spectral measuring apparatus. Further, the near infrared excitation wavelength is suitable for measurement of a vital substance since the quantum efficiency of fluorescence generated from the vital substance is small, photon energy is smaller than that in the visible region, and damage of the sample is small.

The spectroscope of the photoreceiving part is prepared from the monodispersive spectroscope and the polychrometer is formed by employing the multi-channel detector of the photodiode array for detecting Raman scattered light separated into its spectral components by the spectroscope, whereby the volume is small and damping of the light quantity is also small. Thus, the overall Raman spectral measuring apparatus can be miniaturized, leading to cost reduction.

When the integrating sphere type scattered light reinforcing holder for making multiple reflection of the excitation light is comprised as the holder for holding the sample cell in the sample part in order to improve Raman scattered light generation efficiency, detection can be made at an excellent S/N ratio.

The automatic analyzer comprising the inventive Raman spectral measuring apparatus is suitable for analyzing a minor vital substance, and can implement measurement at a high speed and in high sensitivity and high accuracy for multiple items at a low cost.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 8A is a front elevational view showing an integrating sphere type scattered light reinforcing holder as an exemplary sample cell holder in a sample part;

FIG. 8B is a plan view of the holder;

FIG. 8C is a right side elevational view of the holder;

FIG. 8D is an exploded perspective of the holder;

DESCRIPTION OF THE PREFERRED EMBODIMENTS

Figure 1:
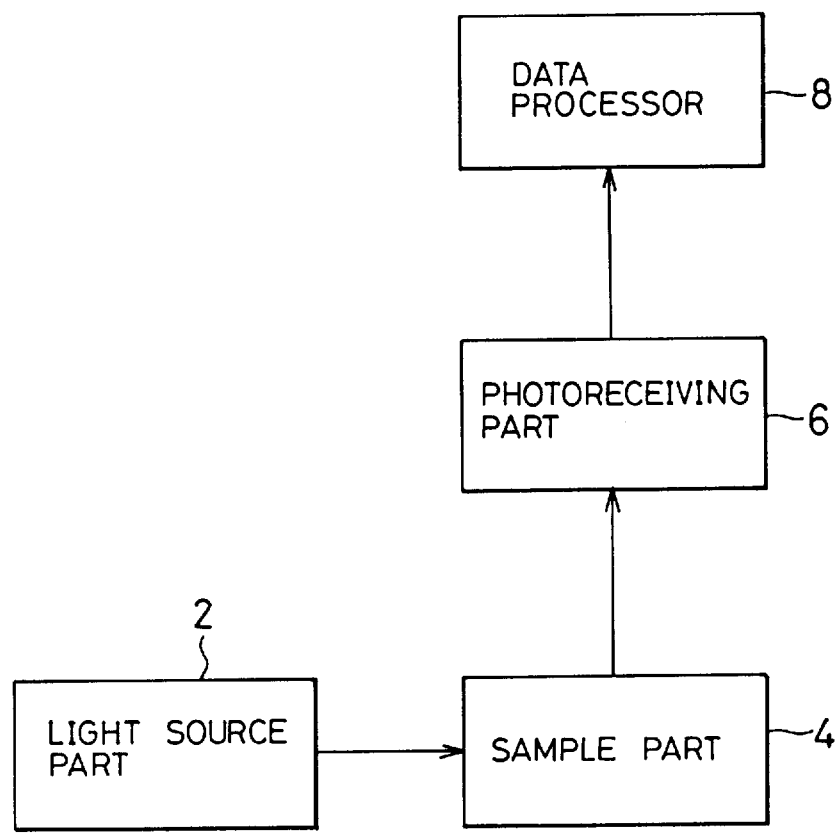
FIG. 1 is a block diagram showing a Raman spectral measuring apparatus according to the present invention.

FIG. 1 schematically illustrates a Raman measuring apparatus according to the present invention. A sample provided on a sample part 4 is irradiated with excitation light from a light source part 2, so that Raman scattered light from the sample is separated into its spectral components and detected in a photoreceiving part 6, and the concentrations of target components in the sample are measured in a data processor 8.

FIGS. 2 to 6 concretely illustrate optical systems in the present invention.

Figure 2:
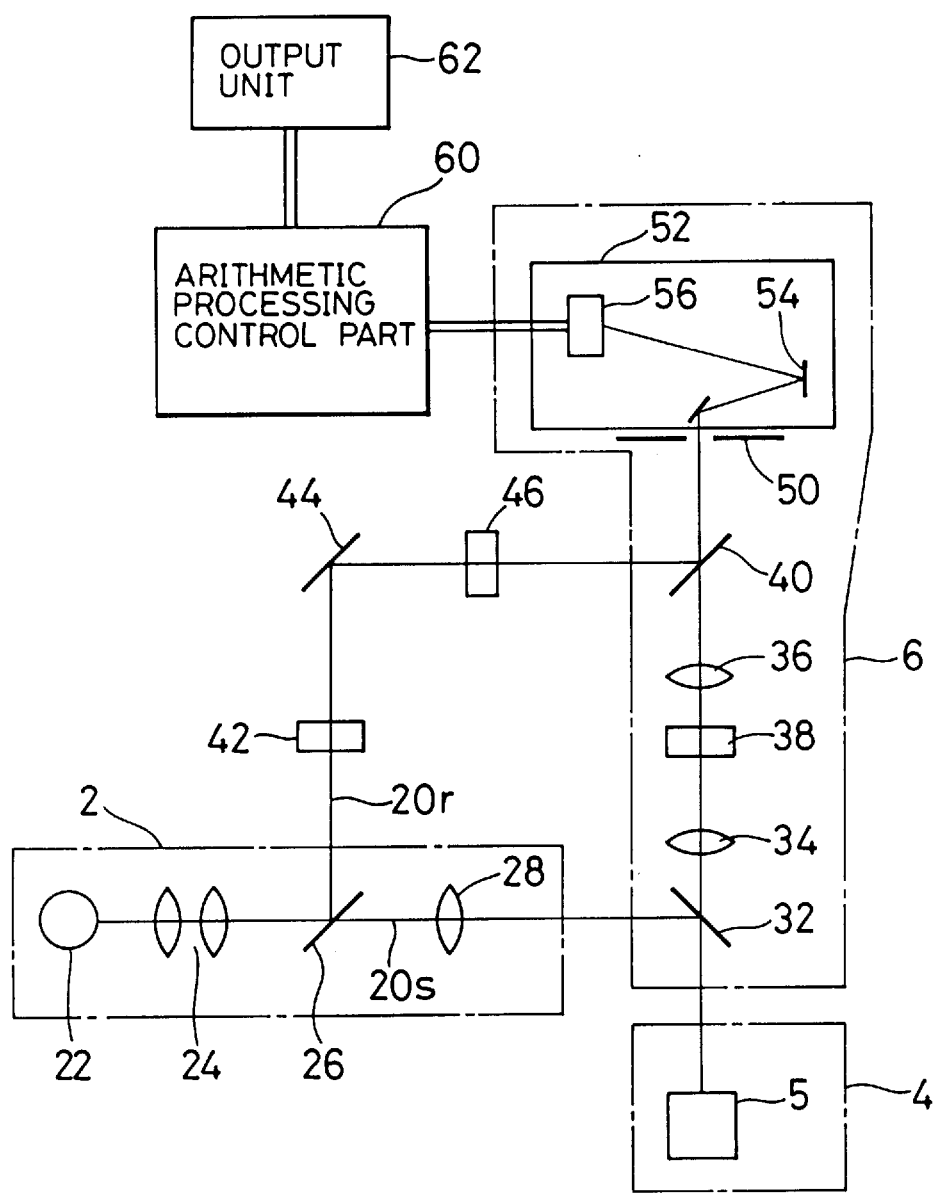
FIG. 2 is an arrangement diagram showing a measuring apparatus of an embodiment employing a holographic notch filter in a photoreceiving part as filter means for receiving target light in a direction of 180 degrees with respect to excitation light for a sample.

FIG. 2 shows an embodiment providing a holographic notch filter including an excitation light wavelength in its notch region or a cut filter shielding an excitation light wavelength and a shorter wavelength side therefrom in a photoreceiving part 6 for receiving Raman scattered light in a direction of 180 degrees with respect to excitation light for a sample.

A laser diode (InGaAs laser diode by SDL, U.S.A.) is provided in a light source part 2 as a light source 22, while a half mirror 26 is arranged as a beam splitter for dividing excitation light from the light source 22 into a sample beam 20s and a correction beam 20r. A light source condensing lens 24 and a convergent lens 28 are arranged in the light source part 2 with a half mirror 26 between, in order to converge the sample beam 20s on a sample cell 5 provided in a sample part 4.

The sample beam 20s from the excitation light source part 2 is reflected by a half mirror 32 which is arranged in the photoreceiving part 6, and applied to a sample in the sample cell 5. The photoreceiving part 6 is provided with condenser lenses 34 and 36, in order to converge Raman scattered light from the sample transmitted through the half mirror 32 on an inlet slit 50 of a spectroscope 52 as target light. Light which is incident upon the photoreceiving part 6 from the sample also includes Rayleigh scattered light in addition to the Raman scattered light. Therefore, a holographic notch filter 38 which is set to include the excitation light wavelength in its notch region is arranged in the photoreceiving part 6 as a filter for removing the same wavelength component as the excitation light and transmitting the Raman scattered light. Such a holographic notch filter is available on Kaiser Optical Systems Inc., U.S.A., for example. The holographic notch filter 38 has characteristics of completely shielding wavelength light included in the notch region and transmitting light of other wavelength regions by at least 80%, for example.

A half mirror 40 is arranged as beam combining means between the condenser lens 36 of the photoreceiving part 6 and the inlet slit 50 of the spectroscope 52, so that the Raman scattered light is transmitted through this half mirror 40 and incident upon the spectroscope 52.

An optical correction adjusting part is set for guiding the correction beam 20r which is divided by the half mirror 26 in the light source part 2 to the half mirror 40 of the beam combining means. An extinction filter 42 for damping the quantity of light, a bandpass filter 46 for shielding wavelength light which is generated in the half mirror 26 of the light source part 2 and a sideband from a laser beam from the light source 2, and a mirror 44 for bending the light path are arranged in the optical correction adjusting part. The correction beam 20r which is guided to the inlet slit 50 through the half mirror 40 by the optical correction adjusting part 8 is condensed on the inlet slit 50 by the light source condenser lens 24.

In order to shield the sideband from the laser beam from both of the sample and correction beams 20s and 20r, the bandpass filter 46 may alternatively be arranged on the light path between the light source 22 and the half mirror 26.

The Raman scattered light from the sample and the correction beam 20r which is guided from the optical correction adjusting part 8 are guided onto the same optical axis in the half mirror 40, to be guided to the spectroscope 52 through the inlet slit 50. The spectroscope 52 is formed by a polychrometer comprising a single diffraction grating 54 and a multi-channel photodetector, and comprises a plane mirror for reflecting light incident through th inlet slit 50, a concave diffraction grating 54 for separating the incident light guided by the plane mirror into its spectral components, and a photodiode array detector 56 provided with a plurality of photodetecting elements along the direction of dispersion of the diffraction grating 54 for simultaneously detecting the spectral components separated by the diffraction grating 54 over a prescribed wavelength region.

Numeral 60 denotes an arithmetic processing control part which controls the operations of the respective parts and processes signals detected by the photodetector 56. This arithmetic processing control part 60 also includes a function for correcting a detected intensity of the Raman scattered light on the basis of a detected intensity of an excitation light component in a spectrum which is detected by the photodetector 56, and operates a Raman scattered light spectrum in which fluctuation of the light source is corrected and performs qualification and determination of a sample from the Raman scattered light intensity. Numeral 62 denotes an output unit such as a printer or a display outputting data processed in the arithmetic processing control part 60.

In the embodiment shown in FIG. 2, the holographic notch filter 38 may be replaced with a sharp cut filter having sharp wavelength characteristics for shielding an excitation light wavelength and a shorter wavelength side therefrom.

Figure 3:
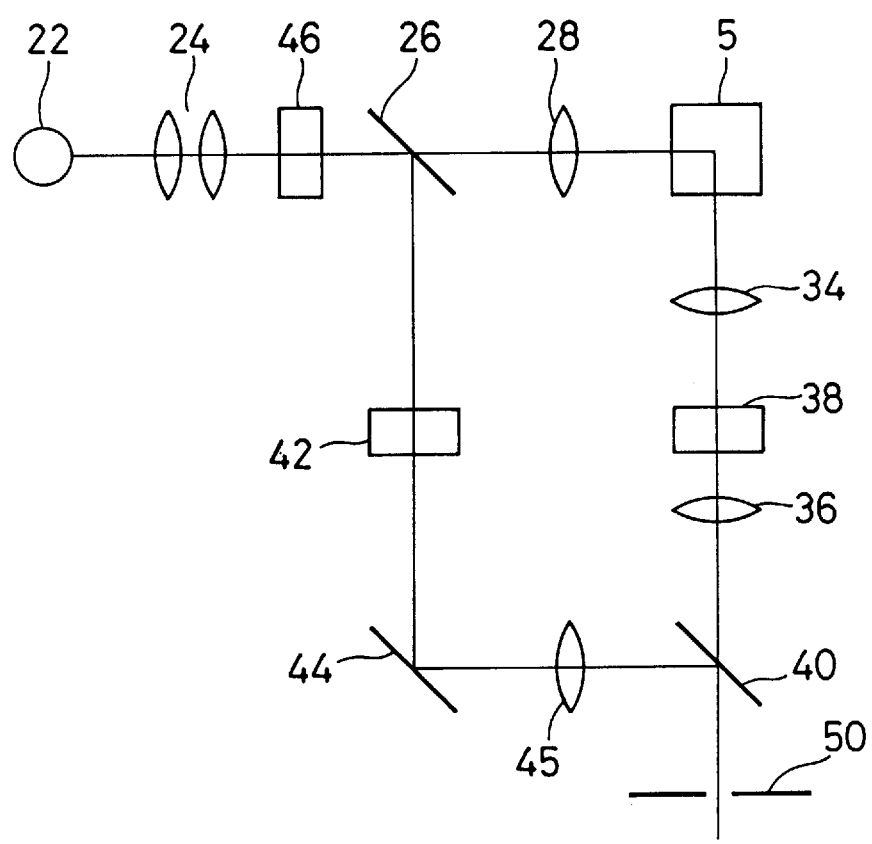
FIG. 3 is an arrangement diagram showing a measuring apparatus of an embodiment employing a holographic notch filter in a photoreceiving part as filter means for receiving target light in a direction of 90 degrees with respect to excitation light for a sample.

FIG. 3 illustrates an embodiment employing a holographic notch filter or a cut filter as filter means of a photoreceiving part 6 similarly to the embodiment shown in FIG. 2. However, this embodiment is adapted to receive Raman scattered light in a direction of 90 degrees with respect to excitation light for a sample. In this case, no half mirror 32 is necessary for irradiating a sample in a sample cell 5 with a sample beam 20s and making scattered light from the sample incident upon a condenser lens 34 of the photoreceiving part 6. The sample beam 20s is converged by a light source condenser lens 24 and a convergent lens 28 of an excitation light source part 2 and directly applied to the sample in the sample cell 5, so that the scattered light from the sample is directly incident upon the condenser lens 34 of the photoreceiving part 6.

While the bandpass filter 46 is arranged on the light path of the optical correction adjusting part 8 in FIG. 2, that in FIG. 3 is arranged on a light path in front of a beam splitter 26 for dividing a beam from an excitation light source into the sample beam and a correction beam in the excitation light source part. It is possible to shield a sideband of a laser beam from both of the sample and correction beams by arranging the bandpass filter 46 on the position shown in FIG. 3. While a condenser lens 45 is further arranged on the light path of an optical correction adjusting part in FIG. 3, this lens 45 is adapted to condense the correction beam on the position of a slit 50 for adjusting the quantity of light, and is not necessary if the quantity of the correction beam is sufficiently high.

Figure 4A:
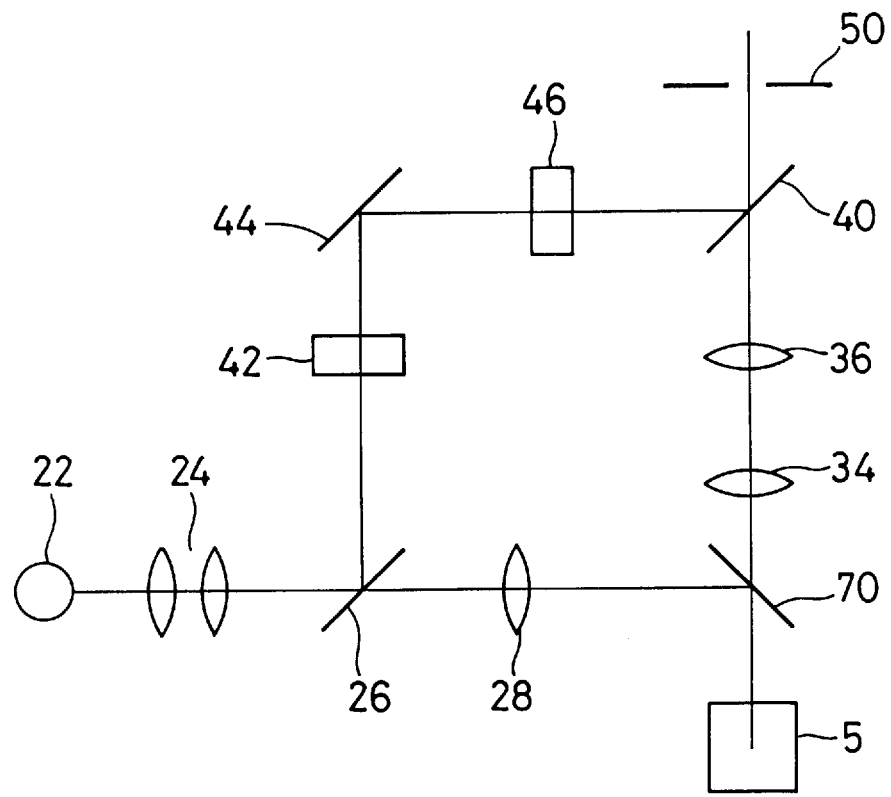
FIG. 4A is an arrangement diagram showing a measuring apparatus of an embodiment employing a holographic beam splitter in a photoreceiving part as filter means for receiving target light in a direction of 180 degrees with respect to excitation light for a sample.

FIG. 4A illustrates an embodiment employing a holographic beam splitter 70 having characteristics of reflecting excitation light and transmitting Raman light as filter means of a photoreceiving part 6 for receiving Raman scattered light in a direction of 180 degrees with respect to excitation light for a sample.

Figure 4B:
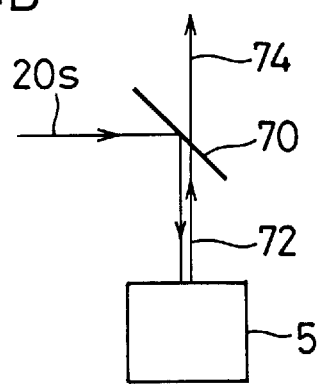
FIG. 4B is a sectional view schematically showing the holographic beam splitter part in the embodiment shown in FIG. 4A.

As shown in FIG. 4B, the holographic beam splitter 70 reflects a sample beam 20s, applies the same to a sample in a sample cell 5, and transmits only Raman scattered light 74 in light 72 from the sample including the Raman scattered light and Rayleigh scattered light for making the same incident upon a condenser lens 34 of the photoreceiving part 6.

Figure 5A:
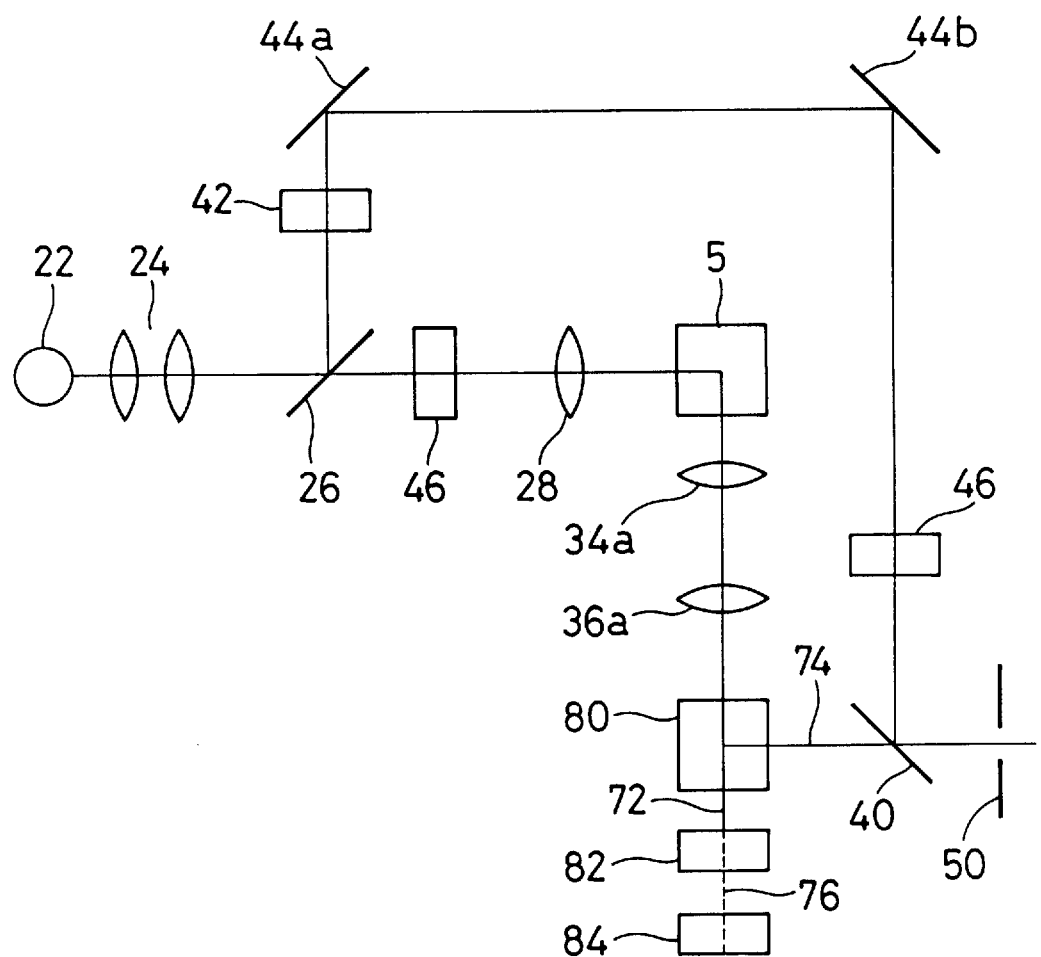
FIG. 5A is an arrangement diagram showing a measuring apparatus of an embodiment employing a bandpass filter for a photoreceiving part as filter means for receiving target light in a direction of 90 degrees with respect to excitation light for a sample.

FIG. 5A illustrates an embodiment employing a bandpass filter 82 having characteristics of transmitting and removing an excitation light wavelength component and reflecting a Raman scattered light component as filter means of a photoreceiving part 6. In this case, Raman scattered light is received in a direction of 90 degrees with respect to excitation light for a sample.

Figure 5B:
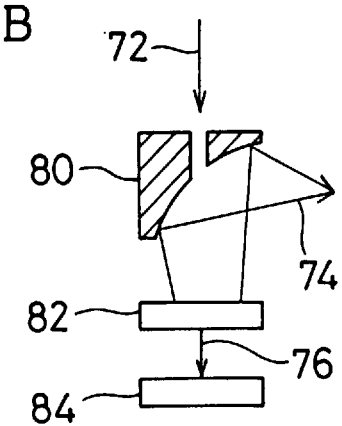
FIG. 5B is a sectional view schematically showing the bandpass filter part in the embodiment shown in FIG. 5A.

As shown in FIG. 5B, the bandpass filter 82 is arranged on a mirror face side of a transmission/condensation mirror 80, while a beam stopper 84 is arranged on an opposite side of the bandpass filter 82 to the transmission/condensation mirror 80. Light 72 from a sample including Raman scattered light and Rayleigh scattered light is condensed by condenser lenses 34a and 36a, to be incident upon the bandpass filter 82 from a back surface of the transmission/condensation mirror 80 through its incidence hole. Rayleigh light 76 is transmitted through the bandpass filter 82 and absorbed by the beam stopper 84, while Raman scattered light 74 is reflected and condensed by the mirror face of the transmission/condensation mirror 80 to be incident upon a spectroscope from an inlet slit 50 through a half mirror 40. Two mirrors 44a and 44b are arranged in an optical correction adjusting part 8, in order to bend a light path by 180 degrees.

Figure 6:
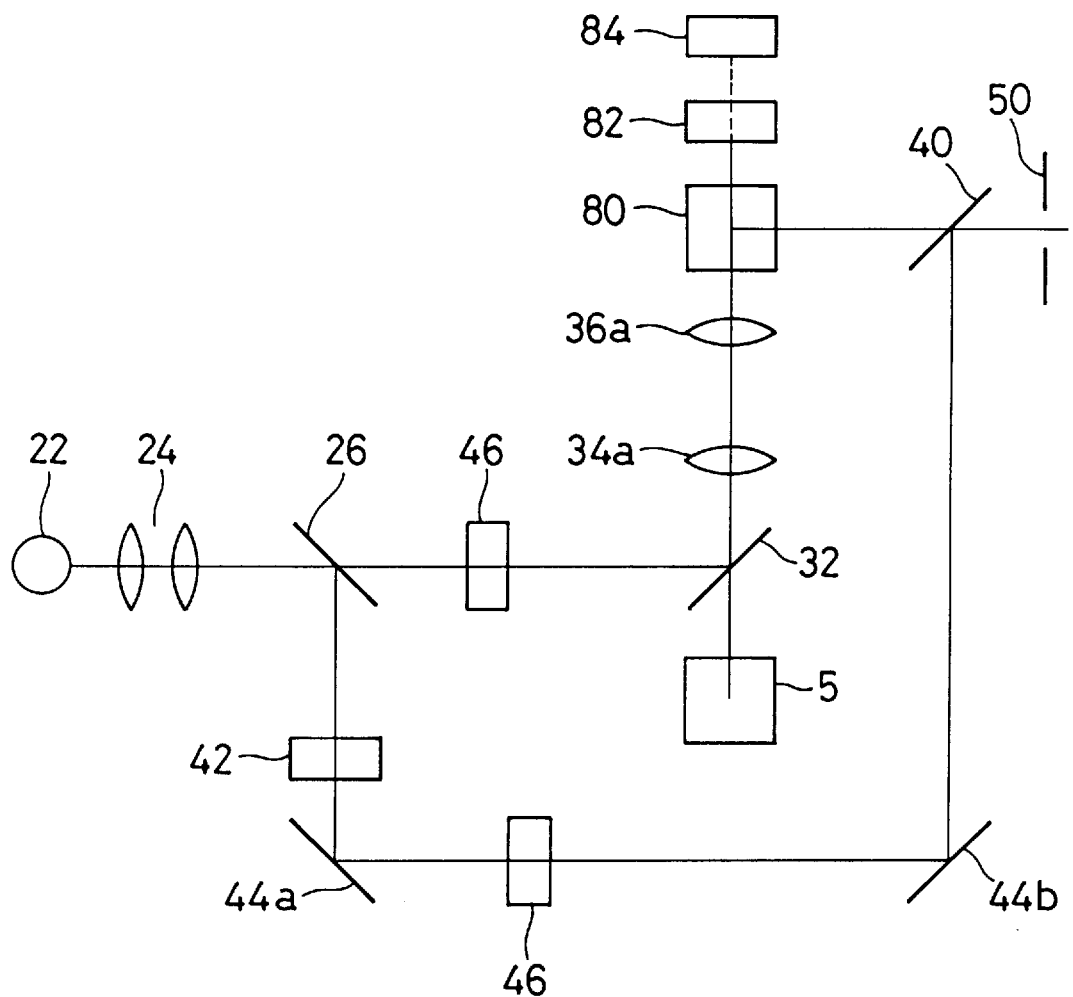
FIG. 6 is an arrangement diagram showing a measuring apparatus of an embodiment employing a bandpass filter for a photoreceiving part as filter means for receiving target light in a direction of 180 degrees with respect to excitation light for a sample.

FIG. 6 illustrates an embodiment employing a bandpass filter 82 having characteristics of transmitting and removing an excitation light wavelength component and reflecting a Raman scattered light component as filter means of a photoreceiving part 6, similarly to FIG. 5. However, this embodiment receives Raman scattered light in a direction of 180 degrees with respect to excitation light for a sample. A half mirror 32 is arranged for applying a sample beam 20s to a sample in a sample cell 5 and making light from the sample incident upon a condenser lens 34a of the photoreceiving part 6.

The direction for receiving the Raman scattered light from the sample is not restricted to that of 90 or 180 degrees, but may be that of another arbitrary angle.

In each of the optical systems shown in FIGS. 2 to 6, part of the excitation light is extracted by the beam splitter of the half mirror 26 and detected simultaneously with the Raman scattered light in order to correct light source intensity fluctuation, whereby the Raman scattered light can be correctly measured even if the intensity of the excitation light from the light source fluctuates. Such correction is not restricted to that utilizing part of the excitation light, but may be performed by detecting Rayleigh scattered light generated from the sample simultaneously with the Raman scattered light. If the intensity of the excitation light from the light source has excellent stability, such correction may be omitted.

Figure 7A:
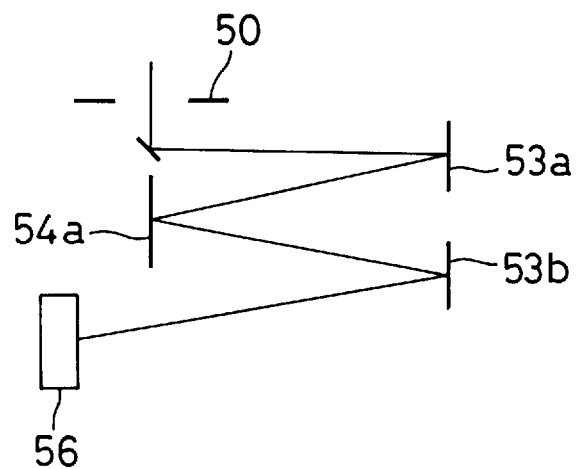
FIG. 7A is a schematic block diagram showing another exemplary monodispersive spectroscope.
Figure 7B:
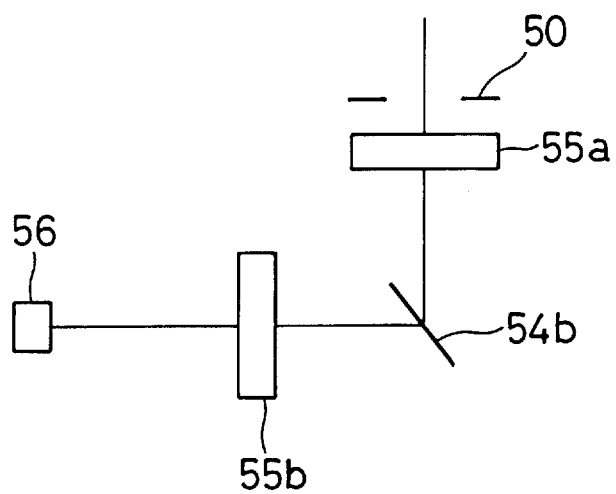
FIG. 7B is a schematic block diagram showing still another exemplary monodispersive spectroscope.

While that employing the concave diffraction grating 54 is illustrated in FIG. 2 as an exemplary monodispersive spectroscope, that shown in FIG. 7A or 7B can alternatively be employed as another monodispersive spectroscope. FIG. 7A illustrates a spectroscope called a Czerny-Turner type spectroscope, in which Raman scattered light incident through a spectroscopic slit 50 or incident light simultaneously incorporating light of an excitation wavelength component for correction and a Rayleigh scattered light component in Raman scattered light is reflected by a plane mirror 51 and a spherical mirror 53a, incident upon a plane diffraction grating 54a to be separated into its spectral components by the plane diffraction grating 54a, and incident upon a multi-channel detector 56 through a spherical mirror 53b. An image of the spectroscopic slit 50 is formed on the detector 56 by the two spherical mirrors 53a and 53b, to be wavelength-dispersed in a direction of arrangement of photodetecting elements.

Referring to FIG. 7B, on the other hand, light incident through a spectroscopic slit 50 is incident upon a transmission type diffraction grating 54b through a condenser lens 55a to be diffracted by the diffraction grating 54b, and forms an image on a multi-channel detector 56 through a condenser lens 55b. In this spectroscope, an image of the spectroscopic slit 50 is formed on the detector 56 by the two condenser lenses 55a and 55b, to be wavelength-dispersed in a direction of arrangement of photodetecting elements.

FIGS. 8A, 8B, 8C and 8D are a front elevational view, a plan view, a right side elevational view and an exploded perspective view showing an integrating sphere type scattered light reinforcing holder, as an exemplary sample cell holder in a sample part.

A cell holder 90 consists of two members 90a and 90b which are superposed with each other, and is provided with a cylindrical cell holding part 92, an integrating sphere part 94 linked with the cell holding part 92, and an inlet/outlet hole 96 for irradiating a cell which is held by the cell holding part 92 with excitation light through the integrating sphere part 94 and taking out scattered light generated from a sample in the cell to the exterior through the integrating sphere part 94.

While a scattered light taking out direction is at 180 degrees to an excitation light incident direction in FIGS. 8A to 8D, an excitation light inlet hole and a scattering light outlet hole may be separately provided so that the excitation light incident direction and the scattered light taking out direction are perpendicular to each other.

Figure 9A:
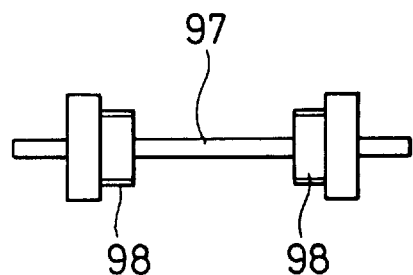
FIG. 9A is a front elevational view showing a flow cell.
Figure 9B:
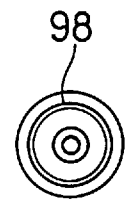
FIG. 9B is a right side elevational view of the flow cell.
Figure 9C:
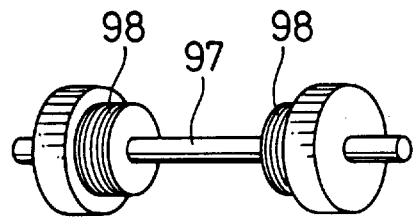
FIG. 9C is a perspective view of the flow cell.
Figure 9D:
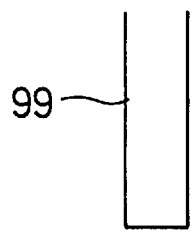
FIG. 9D is a schematic front sectional view showing a disposable cell.

FIGS. 9A to 9C are a front elevational view, a right side elevational view and a perspective view showing a flow cell 97 which is suitably mounted on the cell holder 90 shown in FIGS. 8A to 8D. This flow cell 97, which is made of quartz, is cylindrically formed to be mounted on the cell holding part 92 of the cell holder 90, and flanges 98 are provided on both end portions to be fixed to the cell holder 90. On the other hand, FIG. 9D is a front sectional view showing a disposable cell 99. This disposable cell 99, which is made of plastic, is cylindrically formed to be mounted on the cell holding part 92.

Figure 10A:
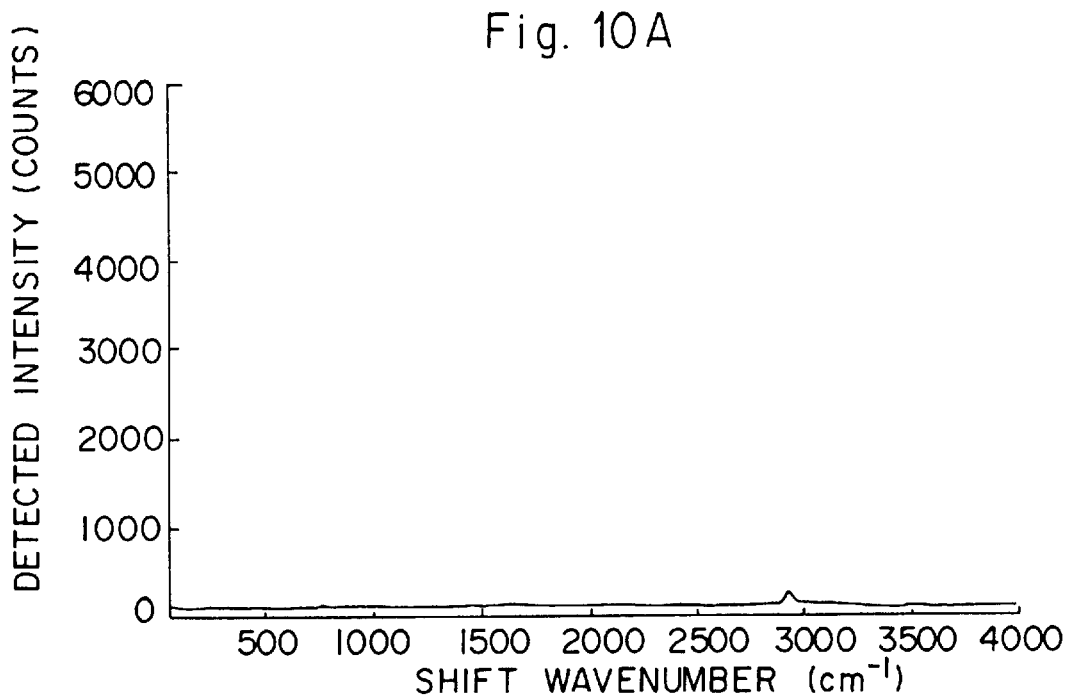
FIG. 10A illustrates a Raman scattering spectrum measured in a measuring apparatus of Example with no integrating sphere type cell holder.
Figure 10B:
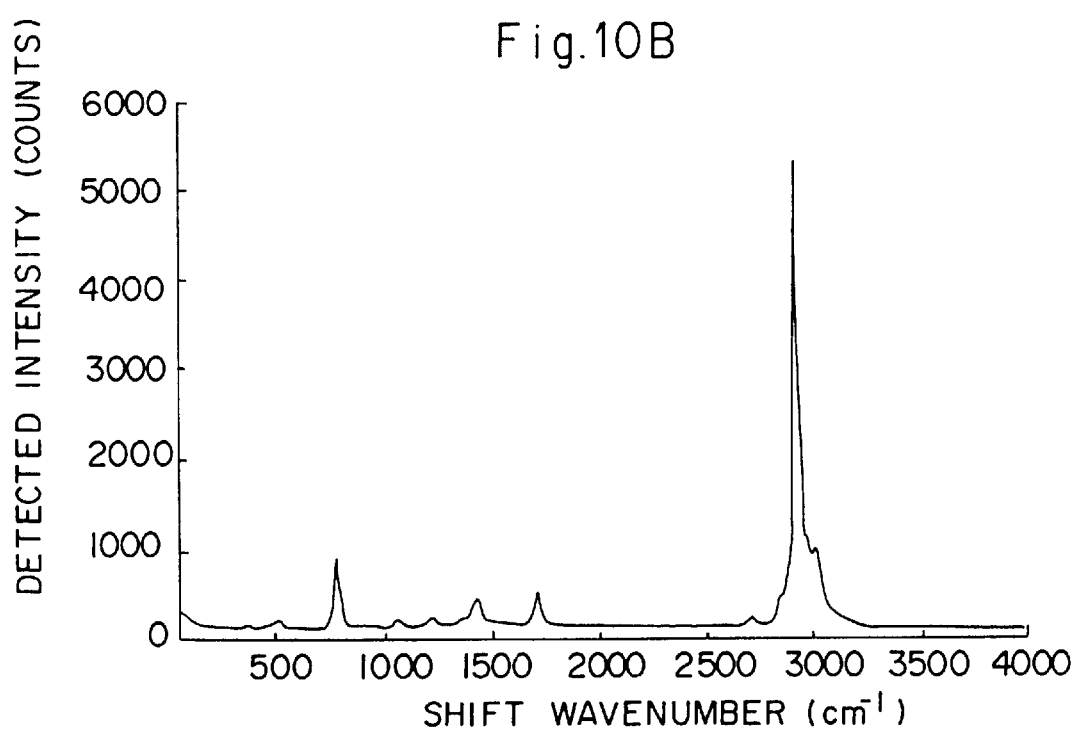
FIG. 10B illustrates a Raman scattering spectrum measured in the measuring apparatus with an integrating sphere type cell holder.
Figure 11A:
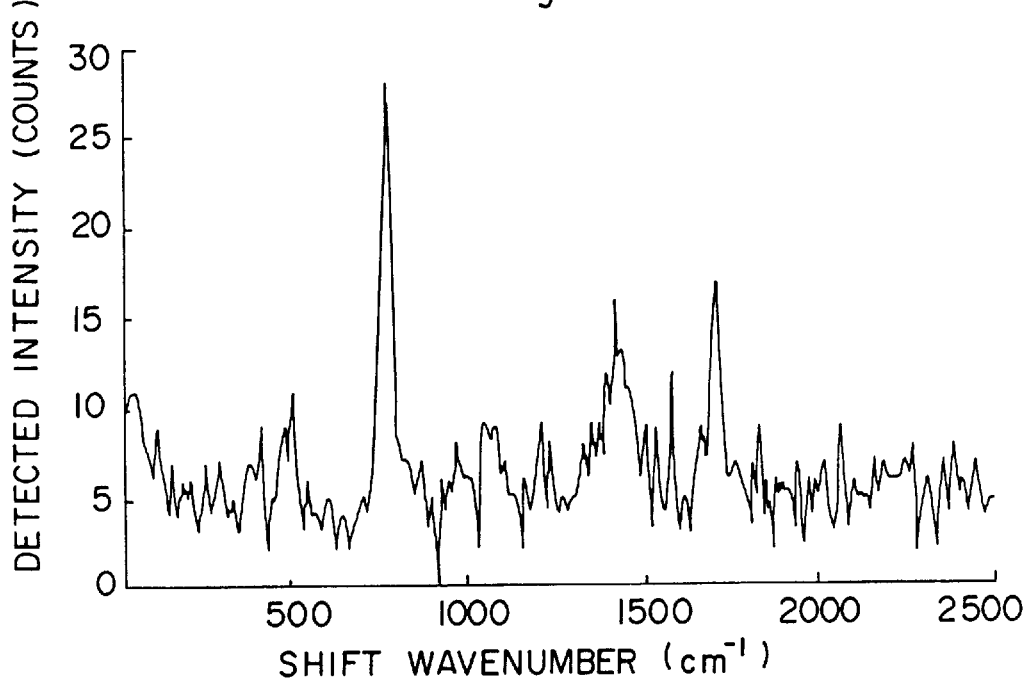
FIG. 11A illustrates the spectrum shown in FIG. 10A while increasing the gain.
Figure 11B:
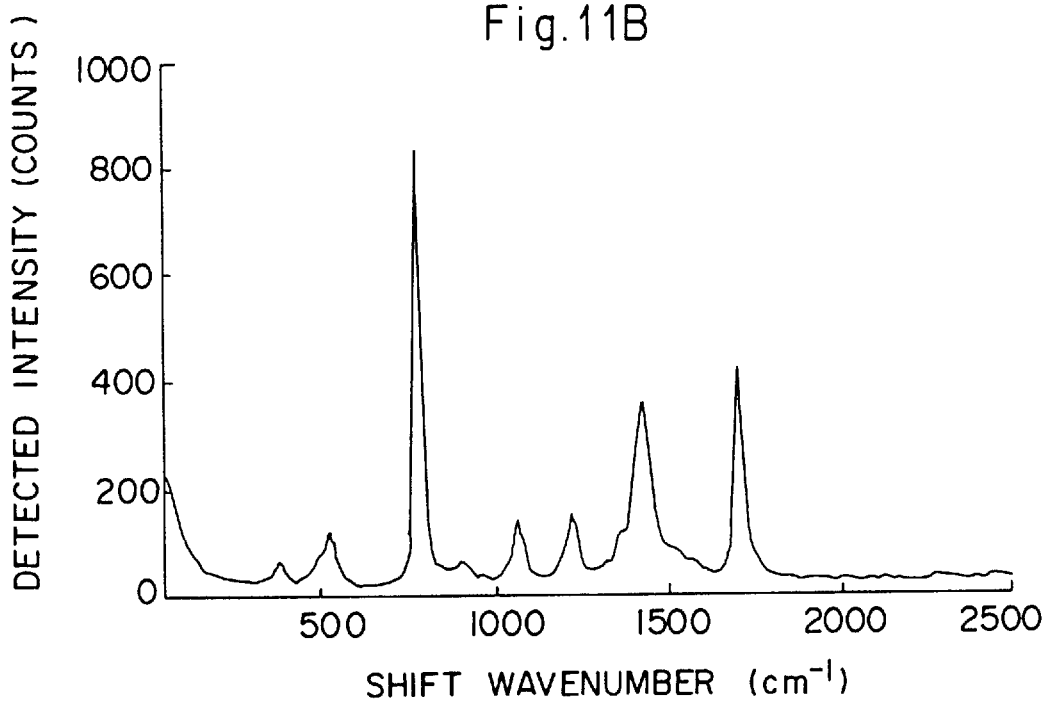
FIG. 11B illustrates the spectrum shown in FIG. 10B while increasing the gain.

FIGS. 10A, 10B, 11A and 11B illustrate results obtained by employing an InGaAs laser diode (product by SDL, U.S.A.) having an oscillation wavelength of 980 nm and an output of 7 mW for a light source and measuring Raman scattering spectra of 99% acetone with the measuring apparatus shown in FIG. 2. FIGS. 10A and 11A show results obtained without the integrating sphere type cell holder 90, and FIGS. 10B and 11B show results obtained with the integrating sphere type cell holder 90. Referring to these graphs, the axes of ordinates show detected intensities, and the axes of abscissas show shift wavenumbers from excitation wavelengths.

The results shown in FIGS. 10A and 10B were obtained by comparing the spectra with each other while expressing the detected intensities on the axes of ordinates on the same scales, and FIGS. 11A and 11B show the same results as those in FIGS. 10A and 10B while increasing the gains for attaining substantially identical peak heights in the range of shift wavenumbers of 0 to 2500 cm$^{-1}$. From the comparison results shown in FIGS. 11A and 11B, it is understood that Raman scattered light is reinforced to about 30 times and the S/N ratio is improved when the integrating sphere type cell holder shown in FIGS. 8A to 8D is employed.

Figure 12:
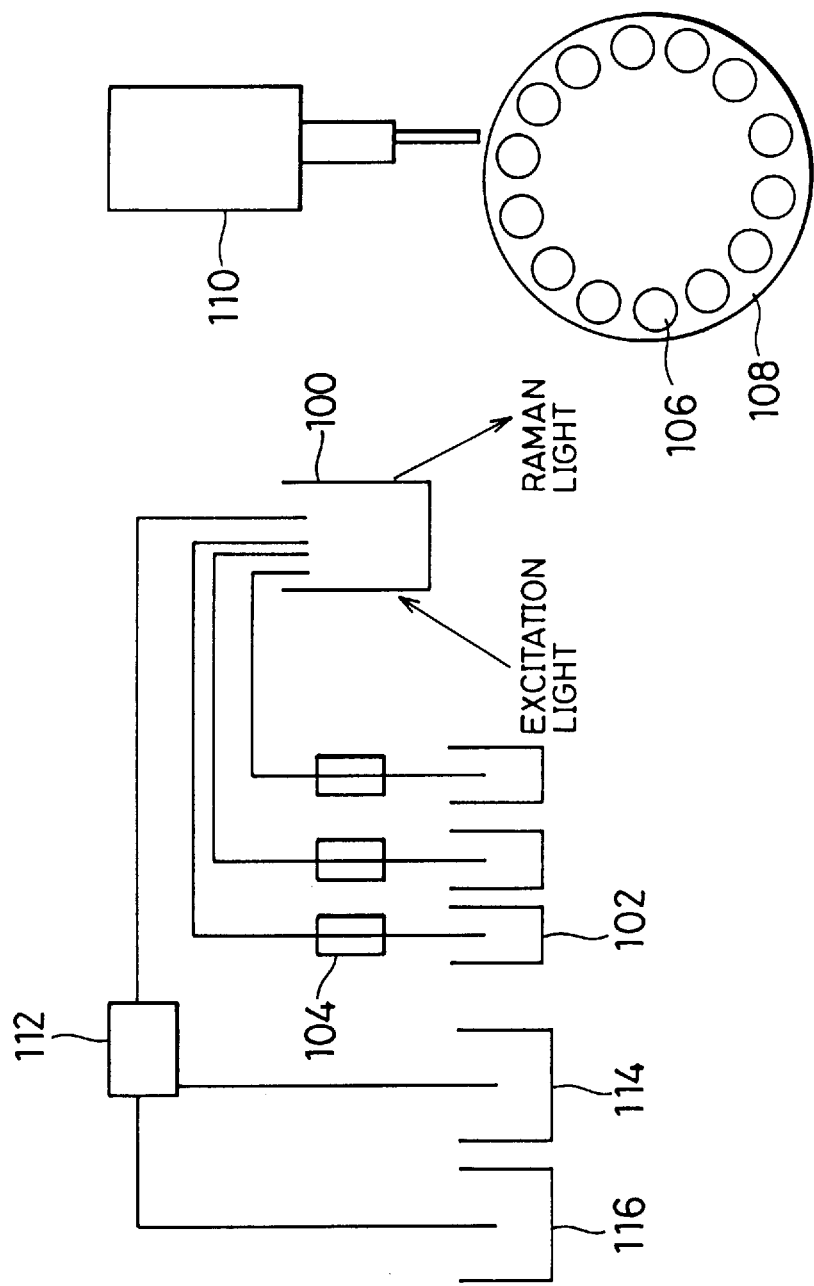
FIG. 12 is a schematic block diagram showing an embodiment of an automatic analyzer utilizing the inventive Raman spectral measuring apparatus as a detecting part.
Figure 13:
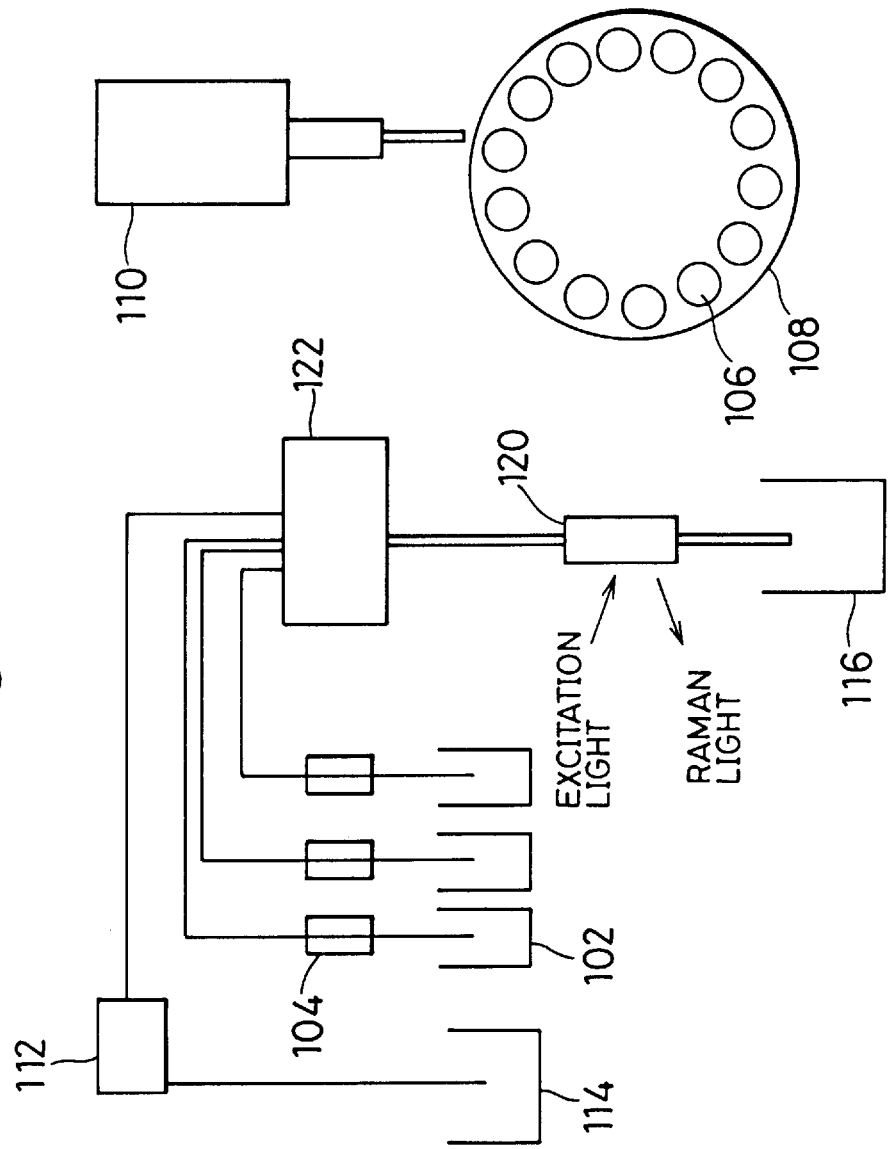
FIG. 13 is a schematic block diagram showing another embodiment of an automatic analyzer utilizing the inventive Raman spectral measuring apparatus as a detecting part.

FIGS. 12 and 13 illustrate automatic analyzers each utilizing the inventive Raman spectral measuring apparatus as a detecting part for optically detecting reaction of a reactive solution in a sample cell.

FIG. 12 shows an exemplary automatic analyzer employing an ordinary cell which is recycled by washing as a sample cell 100. A plurality of types of reagent vessels 102 which are responsive to measured items are provided in order to dispense reagents into the sample cell 100 in response to the measured items, and feed pumps 104 are provided for the respective reagent vessels 102, in order to dispense the reagents in the reagent vessels 102 into the sample cell 100. In order to dispense specimens in the sample cell 100, a turntable specimen rack 108 which is provided with a plurality of specimen containers 106 along its circumference and rotated for locating a prescribed one of the specimen containers 106 on a specimen sucking position and a dispenser 110 for sucking the specimen from the specimen container located on the specimen sucking position and dispensing the same into the sample cell 100 are provided. The specimen rack 108 is not restricted to the turntable type one, but may be prepared from another type one.

In order to wash the sample cell 100, a pump 112 is provided for supplying a washing solution to the sample cell 100 from a washing solution vessel 114 and sucking the washing solution washing the sample cell 100 and discharging the same into a waste liquid vessel 116. The pump 112 is also adapted to discharge a reaction solution from the sample cell 100 into the waste liquid vessel 116 after measurement.

Reagents and specimens are dispensed into the sample cell 100, which in turn is irradiated with excitation light by the inventive Raman spectral measuring apparatus with respect to a reaction solution after a lapse of a prescribed reaction time, so that Raman scattered light by the reaction solution is measured and the concentrations of target components are obtained.

When the sample cell 100 is prepared from a disposable cell scaled with reagents, the mechanisms for reagent dispensation and washing shown in FIG. 12 are unnecessary. On the other hand, a cell supply mechanism is required for supplying the disposable cell corresponding to measured items to a measuring position. After completion of the measurement, the disposable cell may be removed from the measuring position and disposed while containing the reaction solution. However, it is preferable to remove and dispose the cell from the measuring position after discharging the reaction solution so that the measured reaction solution do not flow out. Therefore, the pump 112 and the waste water vessel 116 shown in FIG. 12 are preferably provided.

FIG. 13 shows an exemplary automatic analyzer employing a flow cell as a sample cell 120. A mixer 122 having a switching valve on its outlet for mixing reagents with specimens and reacting the same with each other is provided above the flow cell 120. In order to supply reagents to the mixer 122, a reagent supply mechanism for supplying reagents from reagent vessels 102 by feed pumps 104 and a specimen dispensing mechanism for dispensing specimens contained in specimen containers 106 which are arranged on a specimen rack 108 by a dispenser 110 are provided. In order to wash the mixer 122 and the flow cell 120, a pump 112 is provided for supplying a washing solution from a washing solution vessel 114 to the mixer 122 is provided. The reaction solution after completion of measurement and a washing solution are discharged to a waste liquid vessel 116 through the flow cell 120.

The reagents and the specimens are mixed with each other by the mixer 122, so that the reaction solution is fed from the mixer 122 through the flow cell 120 after a lapse of a prescribed reaction time. While the reaction solution flows through the flow cell 120, the flow cell 120 is irradiated with excitation light by the inventive Raman spectral measuring apparatus, so that Raman scattered light from the reaction solution is measured to obtain the concentrations of target components.

Description is now made on an immunoanalysis method which is suitable for making measurement in the field of a clinical test, biochemical sample measurement, quality control of medicines and the like by using the automatic analyzer described in FIG. 12 or 13.

An immunoanalysis method by Raman scattering measurement is studied as an immunoanalysis method which can make measurement in high sensitivity with no requirement for a number of troublesome chemical treatment operations such as that for labelling antigens or antibodies with a fluorescent substance or a chemiluminescent substance, a B/F separation operation for separating an immune complex (B) making antigen-antibody reaction from and antigen (F) making no antigen-antibody reaction from each other and a washing operation in relation to an immunological analysis method. The wavelength of Raman scattered light is shifted from that of the excitation light by a frequency by internal vibration of the immune complex substance. A formed immune complex can be identified from a Raman spectrum by separating the Raman scattered light into its spectral components and detecting the same, while the added target substance can be determined from the Raman scattered light intensity.

Sample DNA is thermally denatured into single-stranded DNA. Probe DNA is added thereto, the temperature is so reduced that the probe DNA and the sample single-stranded DNA are annealed. A noble metal colloid is added thereto, and irradiated with excitation light, so that surface-enhanced Raman scattering is spectrally analyzed. Weak surface-enhanced Raman scattering takes place if the probe DNA is bonded to the single-stranded DNA, while strong surface-enhanced Raman scattering takes place if the former is not bonded to the latter. A target gene can be detected by this difference.

Concrete Example is now described.

Polyadenine was adjusted to $10^{-5}$ mol/l and polythymine was adjusted to $10^{-6}$ mol/l, $10^{-6}$ mol/l, $10^{-7}$ mol/l and $10^{-8}$ mol/l to be mixed with 0.5 ml of nucleotide each, treated at 90° C. for 5 minutes respectively, and thereafter annealed at 37° C. for 30 minutes.

A mixture obtained by adding 0.1 MHCl to a silver colloid prepared by the Clayton method and adjusting the same to pH 2.7 was taken by 1.9 ml so that 0.1 ml of each of the aforementioned annealed DNA mixed solutions was added thereto, and surface-enhanced Raman scattering was measured. FIG. 17 shows the results. FIG. 18 shows a calibration curve thereof.

The operation of each of the automatic analyzers shown in FIGS. 12 and 13 is now described in more detail.

Figure 14:
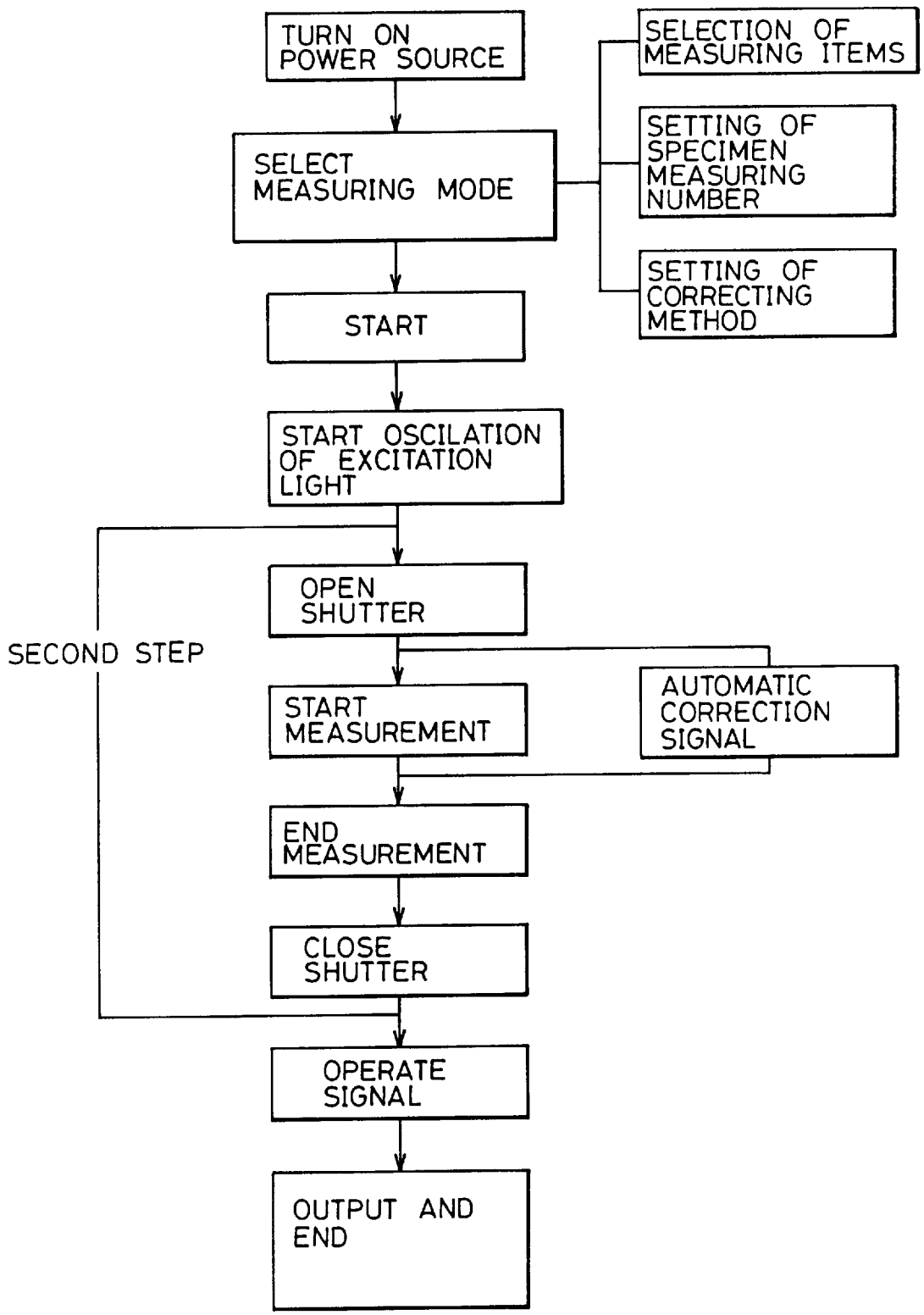
FIG. 14 is a flow chart showing a Raman scattering measuring operation by the Raman spectral measuring apparatus in either embodiment of the automatic analyzer.

FIG. 14 is a flow chart showing an operation called a first step of measuring a reaction solution in the sample cell by the inventive Raman spectral measuring apparatus.

The power source for the apparatus is turned on, and a measuring mode is selected and set. Measuring modes include selection of measured items, setting of a specimen measurement number, and setting of a correct ion method. A method of incorporating part of excitation light in the same multi-channel photodetector for correcting fluctuation of the light source as in the optical system shown in FIG. 2, a correcting method of incorporating Rayleigh scattered light in the same multi-channel photodetector, or a method performing no correction of light source intensity can be selected as the correcting method.

When a start button is pushed to start measurement, excitation light starts oscillation in the Raman spectral measuring apparatus serving as a detecting part.

Reagents and specimens are dispensed in the sample cell, and a shutter between the light source part and the sample cell is opened after a lapse of a constant reaction time so that the reaction solution in the sample cell is irradiated with excitation light, raman scattered light is generated from the reaction solution and detected by the detecting part, and thereafter the shutter between the light source part and the sample cell is closed to complete single measurement. Denoted as a second step are dispensation of reagents and specimens in the sample cell in a reaction part, reaction solution discharge, sample cell washing and the like, as described later with reference to FIGS. 15 and 16. After measurement for the set specimen measurement number is completed, signal operation processing of the detected Raman scattered light is performed so that operation results are outputted and the measuring operation is completed.

Figure 15:
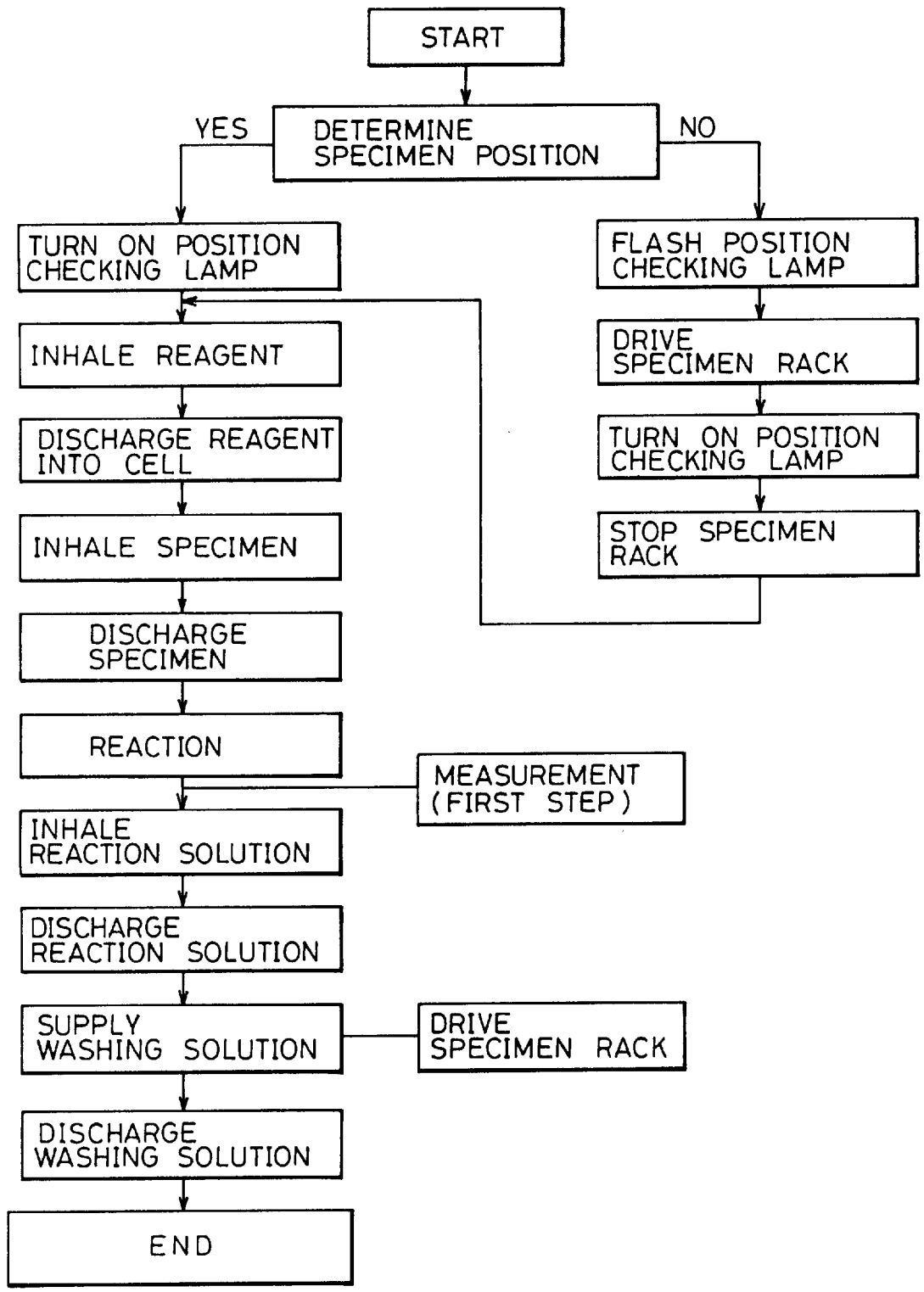
FIG. 15 is a flow chart showing an operation of either embodiment of the automatic analyzer employing an ordinary or flow cell as the sample cell.

FIG. 15 shows the operation in the reaction part in case of preparing the sample cell from an ordinary cell which is washed and recycled or a flow cell.

When the start button is pushed to start measurement, the reaction part determines whether or not a prescribed specimen is located on the specimen sucking position of the specimen rack 108, so that a lamp indicating the result of such specimen checking is flashed, the specimen rack 108 is driven to locate the prescribed specimen on the specimen sucking posit ion, and the position checking lamp is turned on to display that dispensation of the specimen is possible if the determination is of no. A reagent responsive to the measured item is inhaled by the feed pump 104 and discharged to the sample cell 100 or the mixer 122, to start reaction. After a lapse of a constant reaction time, the reaction solution is supplied in the sample cell 100, or from the mixer 122 to the flow cell 120 in case of a flow cell, so that Raman scattered light is measured by the procedure shown in FIG. 14.

In case of an ordinary cell, the reaction solution is thereafter inhaled by the pump 112 and discharged to the waste liquid vessel 116, so that thereafter the washing solution is supplied to the sample cell 100 by the pump 112, and the washing solution is then discharged from the sample cell 100 into the waste liquid vessel 116 after washing. In case of a flow cell, on the other hand, the washing solution is discharged from the mixer 122 to the waste liquid vessel 116 through the flow cell 120 by the pump 112. The specimen rack 108 is driven during washing of the sample cell 100 or washing of the mixer 122 and the flow cell 120, so that the next specimen is located on the specimen sucking position.

Figure 16:
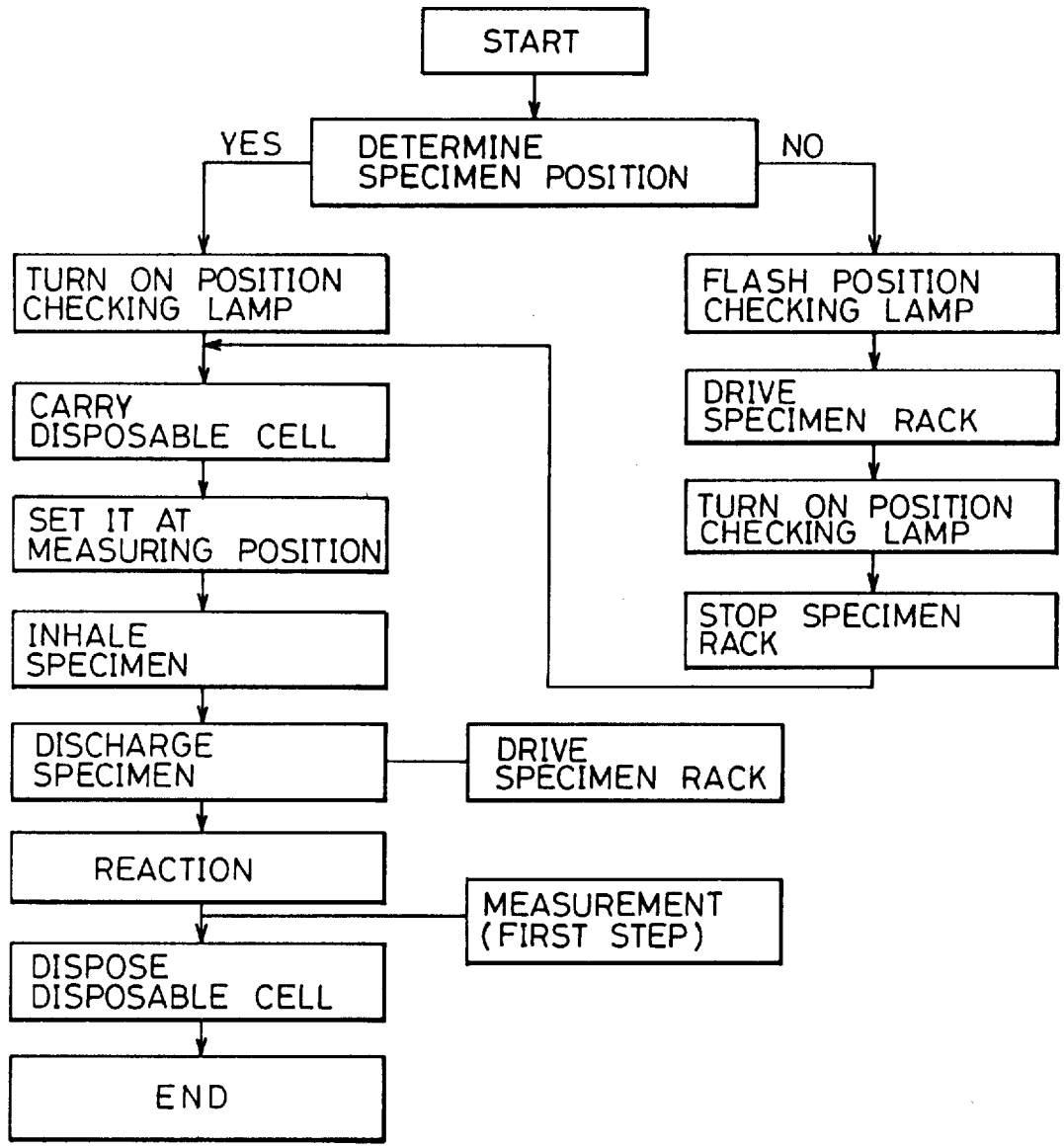
FIG. 16 is a flow chart showing an operation of either embodiment of the automatic analyzer employing a disposable cell as the sample cell.

FIG. 16 illustrates the operation of the reaction part in case of a sample cell prepared from a disposable cell. In this example, it is assumed that the disposable cell is sealed with a metal colloid labelling reagent. Therefore, no reagent is dispensed into the sample cell. When the start button is pushed to start measurement and a prescribed specimen is located on the specimen sucking position in this case, the disposable cell is set on a measuring position and the specimen is dispensed for starting reaction. After a lapse of a constant reaction time, Raman scattered light is measured in the disposable cell on the measuring position by the procedure shown in FIG. 14. After the Raman scattered light is measured, the disposable cell is removed from the measuring position and disposed. In a specimen supply mechanism, the specimen rack 108 is driven immediately after dispensation of a specimen into another disposable cell, so that the next specimen is located on the specimen sucking position.

The automatic analyzer according to the present invention is not restricted to that utilized for an immunological analysis method employing antigen-antibody reaction, but may be adapted to irradiate a specimen sample with excitation light without employing a reagent for performing qualification or determination through Raman scattered light from a target component in the specimen.

Although the present invention has been described and illustrated in detail, it is clearly understood that the same is by way of illustration and example only and is not to be taken by way of limitation, the spirit and scope of the present invention being limited only by the terms of the appended claims.

We claim:

1. A Raman spectral measuring apparatus comprising:

a light source part comprising a near infrared semiconductor laser diode having an oscillation wavelength of 800 to 1560 nm as a light source;

a sample part for irradiating a sample with a sample beam from said light source part;

a photoreceiving part comprising a polychrometer which comprises a single diffraction grating for separating Raman scattered light being generated from said sample into its spectral components and a multichannel detector having sensitivity for near infrared region shifted by Raman scattering from the wavelength of said light source for detecting said Raman scattered light being separated into its spectral components by said diffraction grating; and a data processor for calculating the concentration of a target component in said sample on the basis of a detection signal from said photoreceiving part; wherein said multichannel detector is one of a germanium, indium gallium arsenide, and silicon photo detective device.

2. A Raman spectral measuring apparatus comprising:

a light source part comprising a near infrared semiconductor laser diode having an oscillation wavelength of 800 to 1560 nm as a light source;

a sample part for irradiating a sample with a sample beam from said light source part;

a photoreceiving part comprising a polychrometer which comprises a single diffraction grating for separating Raman scattered light being generated from said sample into its spectral components and a multichannel detector having sensitivity for near infrared region shifted by Raman scattering from the wavelength of said light source for detecting said Raman scattered light being separated into its spectral components by said diffraction grating; and a data processor for calculating the concentration of a target component in said sample on the basis of a detection signal from said photoreceiving part; wherein said light source part further comprises a beam splitter for dividing a beam from said light source into said sample beam and a correction beam, said photoreceiving part further comprises filter means for removing the same wavelength component as excitation light from light from said sample, and a beam combining means for guiding a beam being passed through said filter means and said correction beam to said diffraction grating on the same optical axis, and said data processor has functions of obtaining Raman scattered light intensity at a prescribed wavelength from a spectrum being detected by said detector of said photoreceiving part as a measured value and correcting said measured value on the basis of detected intensity of an excitation light component in said spectrum.

3. The Raman spectral measuring apparatus in accordance with claim 2, wherein said filter means is a holographic notch filter including said excitation light wavelength in its notch region.

4. The Raman spectral measuring apparatus in accordance with claim 1, wherein said filter means is a cut filter for shielding said excitation light wavelength and a shorter wavelength side therefrom.

5. The Raman spectral measuring apparatus in accordance with claim 2, wherein said filter means is a bandpass filter having characteristics of transmitting to remove said excitation light wavelength component and reflecting other wavelength components.

6. The Raman spectral measuring apparatus in accordance with claim 2, wherein said filter means is a holographic beam splitter for removing said excitation light wavelength by transmission or reflection.

7. A Raman spectral measuring apparatus comprising:

a light source part comprising a near infrared semiconductor laser diode having an oscillation wavelength of 800 to 1560 nm as a light source;

a sample part for irradiating a sample with a sample beam from said light source part;

a photoreceiving part comprising a polychrometer which comprises a single diffraction grating for separating Raman scattered light being generated from said sample into its spectral components and a multichannel detector having sensitivity for near infrared region shifted by Raman scattering from the wavelength of said light source for detecting said Raman scattered light being separated into its spectral components by said diffraction grating; and a data processor for calculating the concentration of a target component in said sample on the basis of a detection signal from said photoreceiving part; wherein said sample part comprises an integrating sphere type scattered light reinforcing holder as a holder for holding a sample cell.

8. A Raman spectral measuring apparatus comprising:

a light source part comprising a near infrared semiconductor laser diode having an oscillation wavelength of 800 to 1560 nm as a light source;

a sample part for irradiating a sample with a sample beam from said light source part;

a photoreceiving part comprising a polychrometer which comprises a single diffraction grating for separating Raman scattered light being generated from said sample into its spectral components and a multichannel detector having sensitivity for near infrared region shifted by Raman scattering from the wavelength of said light source for detecting said Raman scattered light being separated into its spectral components by said diffraction grating; and a data processor for calculating the concentration of a target component in said sample on the basis of a detection signal from said photoreceiving part;

wherein a sample cell being held in said sample part is a flow cell or a disposable cell.

9. An automatic analyzer comprising a reaction part comprising a sample cell for reacting a specimen and a reagent with each other, and a detecting part for optically detecting reaction of a reaction solution in said sample cell of said reaction part, said detecting part being a Raman spectral measuring apparatus for irradiating said reaction solution in said sample cell with excitation light from a light source part, and separating Raman scattered light from said reaction solution into its spectral components and detecting the same in a photoreceiving part thereby measuring the concentration of a target component in said reaction solution, said light source part comprising a near infrared semiconductor laser diode having an oscillation wavelength of 800 to 1560 nm as a light source, said photoreceiving part comprising a polychrometer which comprises a single diffraction grating for separating Raman scattered light from said reaction solution into its spectral components and a multichannel detector having sensitivity for near infrared region shifted by Raman scattering from the wavelength of said light source for detecting said Raman scattered light being separated into its spectral components by said diffraction grating.

10. The Automatic analyzer in accordance with claim 9, wherein said multichannel detector is one of a germanium, indium gallium arsenide and silicon photo detective device.

11. The Automatic analyzer in accordance with claim 9, wherein said reaction part comprises a specimen dispensing mechanism for dispensing a specimen into said sample cell, a reagent dispensing mechanism for dispensing said reagent into said sample cell, and a washing mechanism for washing said sample cell.

12. The Automatic analyzer in accordance with claim 9, wherein said reaction part comprises a measuring cell supply mechanism for supplying a disposable sample cell being sealed with said reagent to a measuring position, and a specimen dispensing mechanism for dispensing a specimen into said sample cell on said measuring position.

13. The Automatic analyzer in accordance with claim 9, wherein said reaction part comprises a specimen dispensing mechanism for dispensing a specimen into a mixing part, a reagent dispensing mechanism for dispensing said reagent into said mixing part, and a flow cell serving as said sample cell being fed with said reaction solution from said mixing part.

* * * * *